United States Patent [19]

Roth et al.

[11] Patent Number: 5,640,234

[45] Date of Patent: Jun. 17, 1997

[54] OPTICAL SENSOR FOR DETECTION OF CHEMICAL SPECIES

[75] Inventors: Christoph Roth, Saitama; Yuan Liu, Kawagoe, both of Japan; Werner Prass, Mainz, Germany; Tetsu Yamamoto; Kenji Motosugi, both of Kawagoe, Japan

[73] Assignee: Hoechst Aktiengesellschaft, Frankfurt, Germany

[21] Appl. No.: 545,631

[22] PCT Filed: May 31, 1994

[86] PCT No.: PCT/EP94/01768

§ 371 Date: Nov. 7, 1995

§ 102(e) Date: Nov. 7, 1995

[87] PCT Pub. No.: WO94/28395

PCT Pub. Date: Dec. 8, 1994

[30] Foreign Application Priority Data

Jun. 2, 1993 [JP] Japan .................. 5-131975

[51] Int. Cl.$^6$ .................................................. G01N 21/41
[52] U.S. Cl. .................... 356/128; 356/382; 250/227.14; 385/12; 385/141
[58] Field of Search ................................. 356/128, 382; 250/227.14, 227.18; 385/12, 141

[56] References Cited

U.S. PATENT DOCUMENTS 4,270,049 5/1981 Tanaka et al. .
4,373,768 2/1983 Clark ................................. 356/44
5,082,629 1/1992 Burgess et al. .................. 356/128
5,120,131 6/1992 Lukosz ............................. 356/351
5,513,913 5/1996 Ball et al. ......................... 356/32

FOREIGN PATENT DOCUMENTS 0 481 440   4/1992   European Pat. Off. .
0 487 992   6/1992   European Pat. Off. .
0 584 005   2/1994   European Pat. Off. .

OTHER PUBLICATIONS

Reuter et al., "Monitoring Humidity by Polyimide Light-guides", *Appl. Phys. Lett.* 52(10): 778–779, 7 Mar. 1988.

Patent Abstracts of Japan 17(290): (P–1549) 3 Jun. 1993 & JP,A,05 019 123 (Asahi Seisakushiyo) 29 Jan. 1993.

*Primary Examiner*—Richard A. Rosenberger
*Attorney, Agent, or Firm*—Curtis, Morris & Safford, P.C.

[57] ABSTRACT

Disclosed and claimed is an optical sensor for the detection of chemical species. The optical sensor includes an optical waveguide having a guiding thin film. The thickness of the refrative index of the guiding thin film changes due to adsorption or absorption of the chemical species or reaction of the chemical species with the guiding thin film. The thickness of the guiding thin film is above the cutoff thickness in the presence of gaseous or liquid chemical species to be detected. And, the thickness of the guiding thin film is below the cutoff thickness in the absence of such chemical species.

9 Claims, 5 Drawing Sheets

OPTICAL SENSOR FOR DETECTION OF CHEMICAL SPECIES

BACKGROUND OF THE INVENTION

This invention relates to an optical sensor useful for detecting, quantifying or differentiating chemical species in gaseous or liquid states, as well as an apparatus for detecting chemical species using said optical sensor.

Various types of optical sensors using planar optical waveguides have been known. For example, Tiefenthaler and Lukosz reported on the use of optical grating couplers as biochemical sensors (J. Opt. Soc. Am., B6 (1989) 209 and Sensors and Actuators, 15 (1988) 273). The sensors make use of the angular resonance condition of the excitation of a certain mode of light in a planar waveguide by a grating coupler. The adsorption of human immunoglobulins on the grating coupler changes the thickness and refractive index of the waveguide and, hence, the coupling angle of the light incident on or emerging from the waveguide. Thus, the measurement system under consideration utilizes the effect that the thickness and refractive index of an optical waveguide change upon adsorption of biochemical molecules on top of the waveguide. Such changes can be detected by measuring the coupling angle in the case where a grating coupler or a prism coupler is used. This detection corresponds to the measurement of effective refractive index of certain modes.

Reuter and Franke reported in Appl. Phys. Lett., 52 (1988) 678 a planar optical waveguide having a birefringent polyimide film for monitoring humidity. Light in TE and TM modes will be launched simultaneously into the planar waveguide by means of a prism coupler. The reported measurement system measures the difference between the effective refractive indices in TE and TM modes. This measurement requires special birefringent films. The output obtained by the measurement is a periodic function of the ambient humidity. If one wants to use the output in a certain application, for example, process control, a complex numerical operation system is necessary.

Also known are various optical sensors that utilize the swelling of thin polymer films due to the absorption or adsorption of gases or liquids. For example, Gauglitz et al. reported on a reflection spectroscopy method for gas or solvent detection via swelling of a polymer film (GIT Fachz. Lab., 7(1990) 889 and Abstracts of 1st European Conference on Optical Chemical Sensors and Biosensors, p. 143 (1992)). The setup for implementing the method uses a white light source and a spectrometer for analyzing spectrally the changes in reflected light.

Nylander et al. reported on a setup using the surface plasmon resonance method for gas detection in Sensors and Actuators, 3 (1982/3) 79. When implementing this method, the resonance condition for surface plasmons is greatly influenced by optical parameters of the polymer film used which, in turn, will change with the surrounding organic vapor.

Butler reported a sensor with a polymer film deposited at an end of a multimode optical fiber (Chemical, Biochemical and Environmental Fiber Sensor II, Proc. SPIE 1368 (1990) 46–54). Upon contacting chemical solvents, the polymer film swells to cause a change in reflectance at the fiber end.

The conventional sensors described above utilize the swelling of thin polymer films and detect it by various methods, including interference enhanced reflection (IER) and surface plasmon resonance for measuring the changes in the thickness or refractive index of the thin polymer film.

SUMMARY OF THE INVENTION

It is an object of the present invention to provide a guiding thin film that is to be used as an optical waveguide in an optical sensor for detecting gaseous or liquid chemical species.

Another object of the invention is to measure the attenuation of light in a certain mode travelling through an optical waveguide.

A further object of the invention is to provide a sensor capable of distinguishing between different chemical species.

A still further object of the invention is to provide an array of optical sensor elements made of the same or different materials for improving the identifiability of chemical species to be detected, correcting for background effects or simultaneously detecting different chemical species.

Yet another object of the invention is to provide a detection system that comprises a light source, a waveguide, couplers for coupling light in and out of the waveguide, and a photodetector to measure the intensity of light.

These objects can be attained by the present invention which comprises an optical sensor for measuring the attenuation of light for certain modes in an optical waveguide. The invention utilizes the fact that the attenuation of light in certain modes originates from the changes in the thickness and/or refractive index of a guiding thin film. In the invention, the guiding thin film interacts with the chemical species to be detected, whereby the thickness and/or refractive index of the film will change. In response to this change, the guiding characteristics of the optical waveguide, namely, the degree of attenuation of light in a certain mode, will change. Generally, the degree of attenuation of light in a given mode can be known by exciting light for the given mode and then measuring either the intensity of light coupled out of the optical waveguide or the intensity of light that could be launched into the waveguide (i.e., the difference between the intensities of incident light and reflected light as measured at the coupler on the entrance side). Therefore, the use of special parts such as a birefringent film is essentially unnecessary for the present invention. The measured intensity of light is proportional to the concentration of the chemical species to be detected over a certain range, so according to the invention, not only can the chemical species of interest be detected for its presence but its concentration can also be measured.

BRIEF DESCRIPTION OF THE DRAWINGS

The above and other objects, features and advantages of the present invention will be apparent from the following detailed description of the preferred embodiments of the invention in conjunction with the accompanying drawings, in which.

DESCRIPTION OF THE PREFERRED EMBODIMENTS

Figure 1:
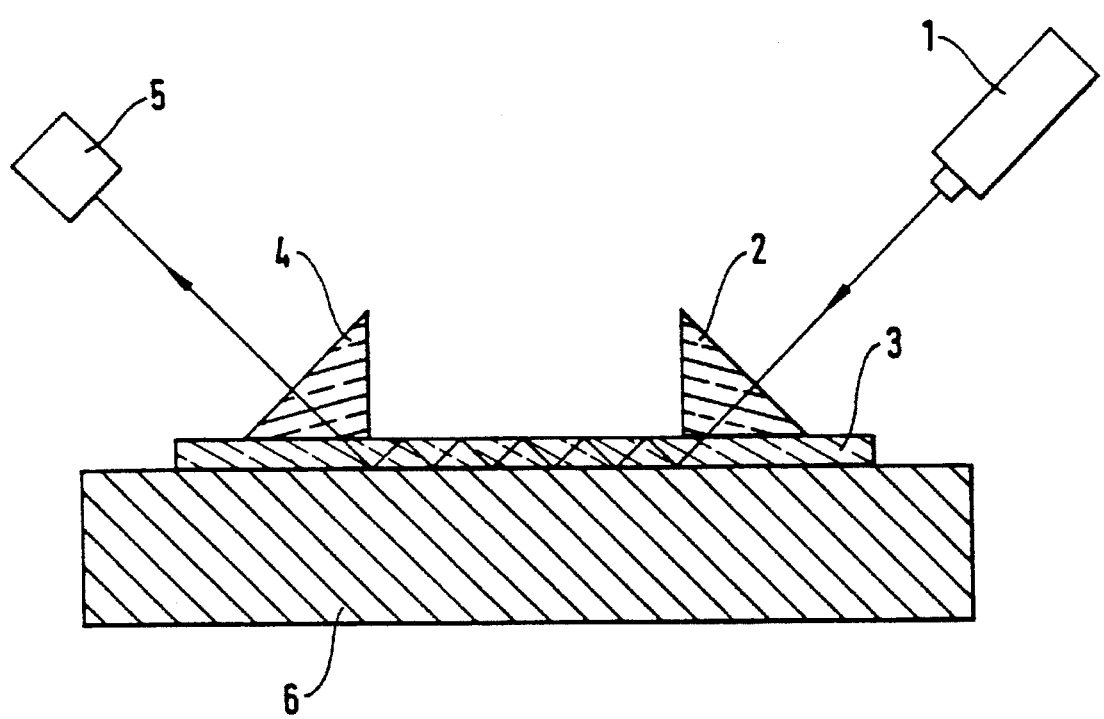
FIG. 1 shows diagrammatically an experimental setup for the apparatus of the present invention.

The optical sensor of the present invention for detecting chemical species comprises a planar optical waveguide having a guiding thin film. Said optical sensor includes couplers disposed on the optical waveguide for coupling light in and out of said waveguide. The chemical species to be detected is adsorbed to or absorbed by the guiding thin film or it reacts with the latter, whereby the thickness or refractive index of the thin film and, hence, its guiding characteristics will change.

When the thickness or refractive index of the guiding thin film changes, the mode of light will change from a guiding mode to a radiating mode or vice versa, whereby the intensity of light travelling through the waveguide varies. To distinguish between guiding and radiating modes, the guiding thin film must be transparent. The change from the guiding to the radiating mode accompanies the decrease in the thickness of the guiding film. In other words, there exists a minimum thickness for the guiding thin film to maintain the guiding mode and this minimum thickness shall hereunder be referred to as the "cutoff thickness".

The guiding characteristics of light for certain modes in the optical waveguide are determined by the thickness and/or refractive index of the guiding film. The thickness of the film varies with the concentration of the chemical species of interest in contact with the surface of the film and the guiding characteristics of light will change accordingly. In the invention, the thickness of the guiding film is selected at such a value that light in a certain of various modes can be guided through the film in a "wet" state (i.e., the guiding mode) but not through the film in a "dry" state (i.e., the radiating mode). In other words, the guiding film is required to be thicker than the cutoff thickness in the "wet" state but thinner than the cutoff thickness in the "dry" state. Here, the "wet" state means the state of the guiding thin film in the presence of the gaseous or liquid chemical species to be detected whereas the "dry" state refers to the state of the film in the absence of such chemical species. It should also be noted that the terms "wet" and "dry" correspond to large and small thicknesses, respectively, of the guiding film, or correspond to high and low refractive indices, respectively, of the film. Therefore, the guiding film in the wet state is thicker than the cutoff thickness and hence is capable of guiding light (in the guiding mode); however, in the dry state, the film is thinner than the cutoff thickness and it is in the radiating mode, in which light radiates its energy outside the film so that its intensity becomes very low at the exit end of the optical waveguide.

The degree of interaction between the guiding thin film and the chemical species to be detected (as exemplified by the changes in the thickness and refractive index of the film) varies with the type of that chemical species. Therefore, the optical sensor of the invention is capable of differential detection of two or more chemical species by making use of the difference in the intensity of outgoing light and/or the response characteristics based on those differences in the interaction.

The guiding thin film to be used in the invention may be of any kind as long as it is capable of reacting with or absorbing or adsorbing one or more chemical species to be detected. For practical purposes, the film can be advantageously prepared from organic or polymeric materials. Examples of the polymeric materials that can be used to make the guiding thin film include vinyl polymers having different side-chain groups, polysiloxanes, polycondensates such as polyesters, polyamides, polyimides, polyurethanes and polyureas. Exemplary organic materials of low molecular weights include phthalocyanines, porphins, porphyrins, organometallic complexes, complexing agents such as cyclodextrins, calixarenes, crown ethers and other crown compounds (e.g., aza crowns) and cryptands.

The substrate for supporting the guiding thin film may be of any kind as long as it is flat. In order to guide light through the film, it must be surrounded by a cladding that is made of a material having a lower refractive index. If the substrate has a lower refractive index than the guiding film, the latter can be directly applied onto the substrate without using claddings. The surface of the guiding film on the side that is not in contact with the substrate may contact either air or, depending on the use, it may be overlaid with a cover layer for protecting the thin film or a superstrate as a cladding. In ordinary cases, the air layer adjacent the guiding thin film will serve as the superstrate.

Take, for example, the case of using a substrate made of a high-index material such as Si; a $SiO_2$ layer may be provided between the Si substrate and a thin organic or polymeric layer.

The guiding thin film can be formed from the above-mentioned materials by any of the known thin-film forming techniques including spin coating, polymer solution casting, melt extrusion and vapor-phase deposition.

The invention encompasses the use of an array of optical sensor elements for detecting chemical species. Stated more specifically, a plurality of units of the optical sensor described hereinabove are assembled to make an optical sensor array. In this case, the guiding thin films and/or substrates may be of the same or different kinds in the individual planar optical waveguides. The array of optical sensor elements enables different chemical species to be detected and/or identified simultaneously.

In addition to the optical sensor described above, the present invention also provides an apparatus for detecting chemical species comprising the sensor itself (including couplers for coupling light in or out of the optical waveguide), a light source for launching light into the sensor, a photodetector for detecting the intensity of incident light and/or emerging light, and a peripheral electric circuit.

Useful light sources include a semiconductor, a solid laser such as a Nd:YAG laser, a gas laser such as a He-Ne laser, a dye laser, a light-emitting diode, etc. Any couplers can be used as long as they are capable of coupling light into or out of the planar optical waveguide, as exemplified by a prism coupler, a grating coupler and a fiber optical coupler. The photodetector is used to measure the intensity of the incident light and/or the intensity of light emerging from the planar optical waveguide and may be exemplified by a photodiode, a phototransistor, a photoconductor, a photoelectric tube, a photomultiplier tube and other devices that are capable of converting the intensity of light to electric signals. The peripheral electric circuit has means for processing and amplifying the electric signals from the photodetector and outputting the result to a recorder. The peripheral electric circuit may also include means such as an alarm for signaling the presence of hazardous substances such as toxic, burnables or flammables substances as detected by the sensor, and/or means for isolating those substances, for example, means for turning on or off switches or pipelines.

An embodiment of the apparatus of the invention for detecting chemical species is shown in FIG. 1. Light from a light source 1 is coupled to a planar optical waveguide via a prism coupler 2. If the light emitted from the light source is not polarized, it is desirably polarized by a suitable polarizer such as a polarizing plate. The planar optical waveguide comprises a guiding thin film 3 and a substrate 6. If desired, a cladding may be provided between the thin film 3 and the substrate 6. The incident light travels through the guiding thin film 3 and emerges therefrom as it is coupled by another prism coupler 4 and the intensity of the outgoing light is measured with a photodetector 5. The two prism couplers are adjusted for their coupling angle in such a manner that light for a certain mode will be excited in the planar optical waveguide. The two prism couplers are typically spaced apart by a distance of about 1 to 100 mm. The chemical species to be detected will flow over the guiding thin film 3 between the two prism couplers. The thickness of the guiding film depends on various parameters including the kind of the chemical species to be detected, the kind of the material which constitutes the film, the mode of light being guided and/or the kind of the substrate to be used; the thickness of the film ranges typically from about 0.1 to 100 μm, preferably from 0.5 to 10 μm.

When the chemical species to be detected flows over the guiding thin film, the interaction between the two (i.e., adsorption, absorption or reaction) will change the guiding characteristics of the film.

This causes a change in the intensity of outgoing light, which is measured as a change in the signal from the photodetector. This is how one can determine whether the chemical species to be detected is present in the gas or liquid under analysis.

The intensity of outgoing light is proportional to the concentration of the chemical species of interest over a certain range and this fact may be used to enable the quantitation of the chemical species. To this end, chemical species having various concentrations are allowed to pass over the optical sensor in the apparatus of the invention and the intensity of light is measured for each passage, thereby establishing a calibration curve to express the relationship between concentration and light intensity.

Another way to measure the attenuation of light in a certain mode is to excite the light that is coupled to the planar optical waveguide by means of the coupler and then measure the intensity of light emerging from the planar waveguide. Alternatively, one may measure the intensity of the light coupled to the planar waveguide. This can be done by, for example, measuring the intensity of the light reflected from a coupler such as a prism or grating coupler on the entrance side and then subtracting the measured intensity from the intensity of the light incident on the coupler.

A beam splitter may be used to split the light from the light source in the present invention. A portion of the thus split light is used as reference light while the other portion is coupled via the coupler to the optical waveguide. In this case, two photodetectors are used, one for measuring the intensity of the reference light and the other for measuring the intensity of light emerging from the planar waveguide. The final output will be expressed as the intensity ratio between the light emerging from the planar waveguide and the reference light. This procedure can be omitted if the intensity of the light from the light source is reasonably stable.

In the case where light is to be guided in several different modes through the planar waveguide, the couplers must have means capable of distinguishing between the modes of light to be coupled. If prism or grating couplers are to be used, the resonance condition for the excitation of light in a certain mode depends on the coupling angle of the light. Therefore, the intensities of light in various modes can easily be distinguished by measuring the intensity of light at different coupling angles.

The invention encompasses the use of suitable optical members for splitting, guiding, focusing or collimating the light to the optical waveguide and/or photodetector.

The optical sensor of the invention is capable of detecting chemical species irrespective of whether it is gaseous or liquid. Further, the sensor has an extremely high sensitivity, wide dynamic range and high response speed. Yet, the sensor uses only of inexpensive components. The optical sensor of the invention is applicable to various fields including process control, quality control and the detection of gas or liquid leakage. A particularly advantageous application of the sensor is where high-sensitivity performance and low cost are required, as exemplified by environmental monitoring for measuring the pollution of air or water. It should also be mentioned that the sensor of the invention is inherently explosion proof and can even be used in environments involving the risk of explosion.

In the following examples, several preferred embodiments are described to illustrate the invention. However, it is to be understood that the invention is not intended to be limited to the specific embodiments.

EXAMPLE 1

Figure 2:
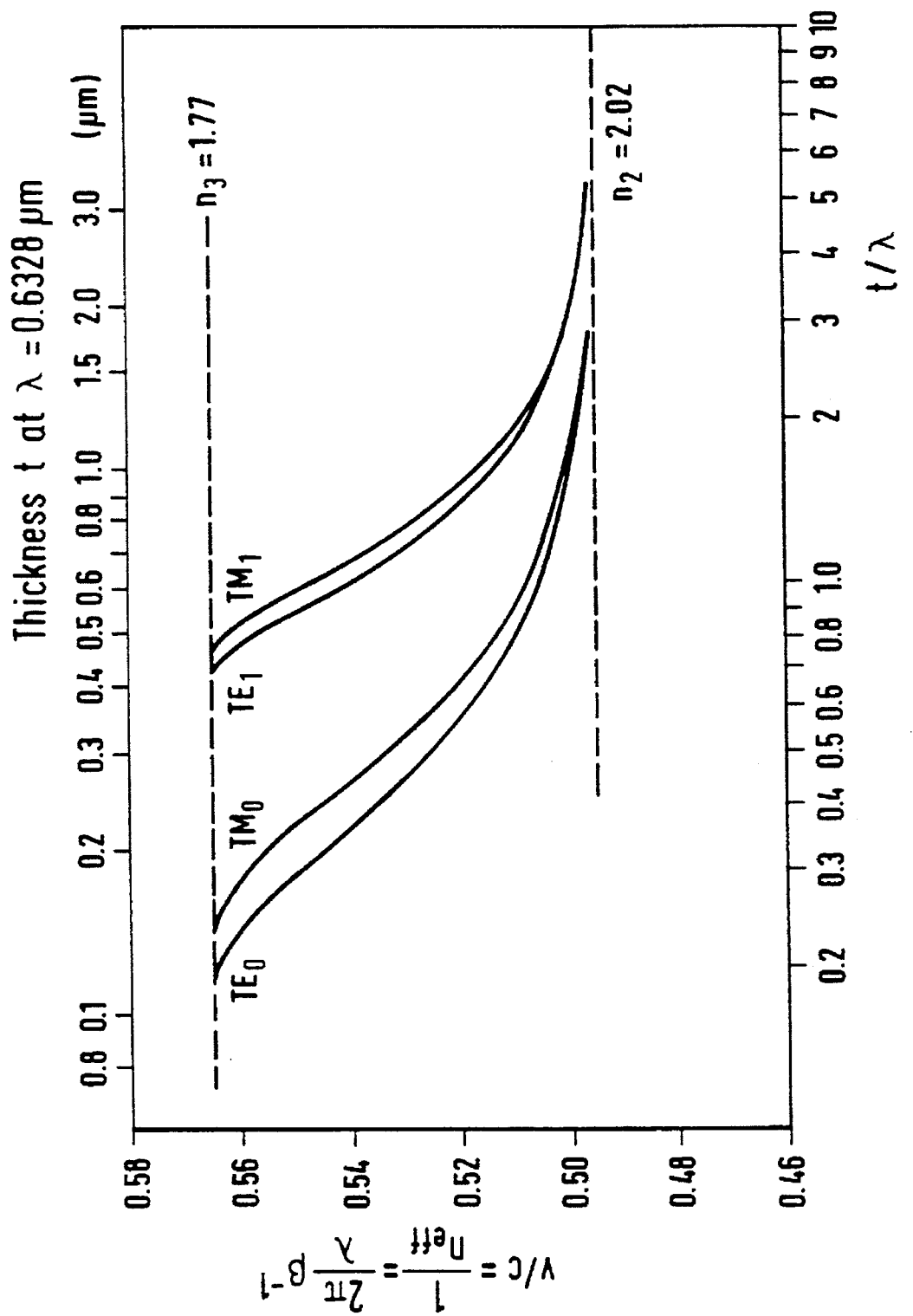
FIG. 2 is a graph showing dispersion curves for light in TE and TM modes.

The cutoff value for the thickness of a guiding thin film was determined in this example. A ZnO substrate was overlaid with a guiding thin sapphire film to prepare an optical waveguide. FIG. 2 plots the velocity of light in TE and TM modes versus the thickness of the guiding film. The wavelength of the light was 632.8 nm. The vertical axis of the graph in FIG. 2 plots the velocity of light in TE or TM modes travelling through the guiding thin film relative to the velocity of light in vacuum (v/c); $n_{\it eff}$ denotes the effective refractive index of light in the TE or TM modes; $\beta$ refers to the propagation constant; $n_2$ designates the refractive index of sapphire; and $n_3$ represents the refractive index of the ZnO substrate.

As is clear from FIG. 2, the cutoff thickness of the guiding film exists for each mode of light and light of neither mode will be guided below the cutoff thickness. Given the values of relevant parameters such as the refractive indices of the guiding thin film, the substrate, the cover layer and the superstrate (if present), the value of the cutoff thickness can be calculated from equations (13.2–5) and (13.2–11) in A. Yariv, "Optical Electronics", Saunders College Publishing, 1991, International Edition.

EXAMPLE 2

This example demonstrates an apparatus for detecting the humidity of air. The experimental setup comprised a laser diode emitting at a wavelength ($\lambda$) of 670 nm (ILEE LDA2000), a 30-mm focusing lens, two prism couplers for coupling light into and out of the optical waveguide, and a photodetector available from Anritsu Corp., Tokyo, Japan. The two prism couplers were spaced apart by a distance of about 10 mm. The whole setup was put in a chamber in which values of temperature and humidity are controlled.

A 1:1 copolymer of 2-ethylhexyl methacrylate and styrene was dissolved in cyclohexanone and the solution was spin coated onto a slide glass to construct an optical waveguide. The guiding film had a thickness close to the cutoff value for $TE_1$ mode. In the dry state, the guiding film was too thin to guide light in the $TE_1$ mode. The thickness of the film increased gradually with the increasing humidity in air. The thus swollen film was capable of guiding light in the $TE_1$ mode. Thus, humidity could be measured over a wide range.

Figure 3:
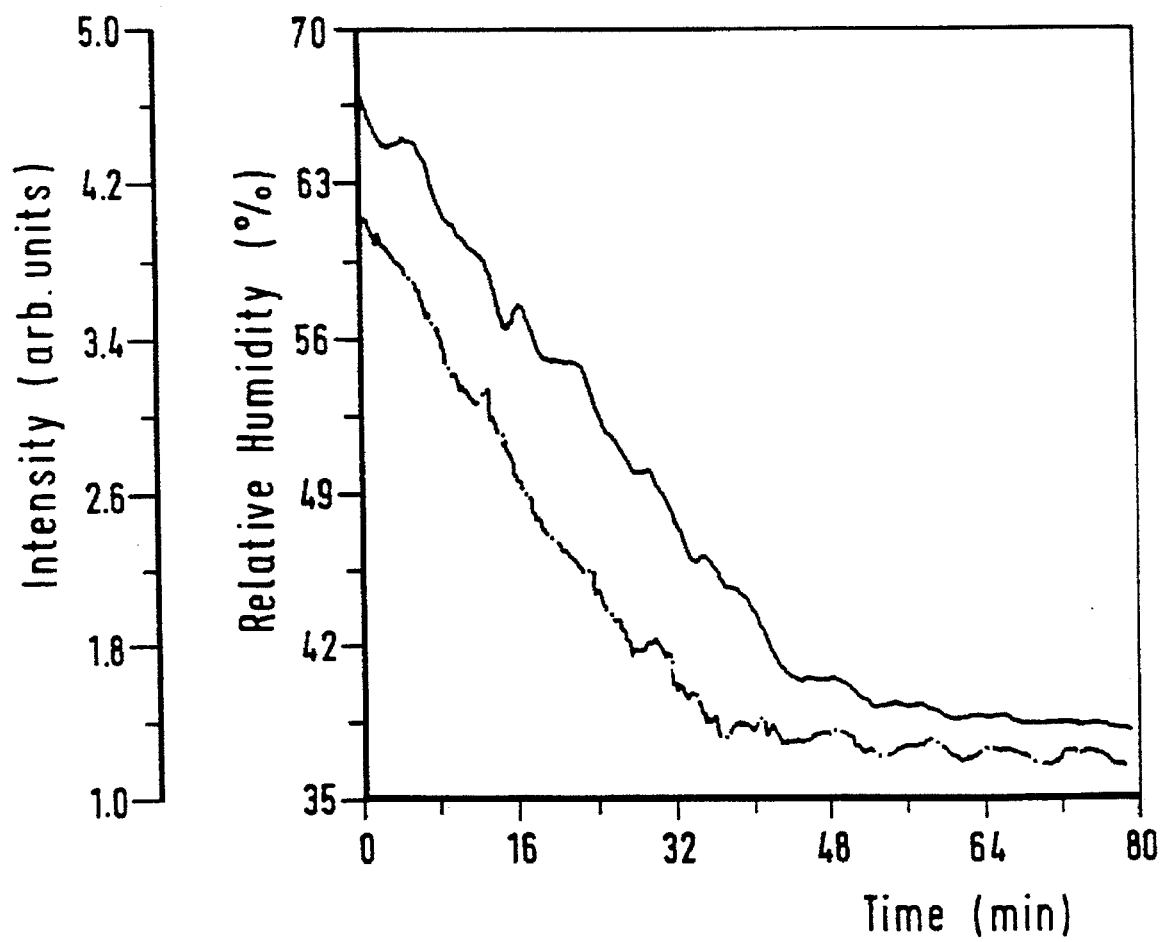
FIG. 3 is a graph comparing the output of the optical sensor of the invention with the humidity of ambient air.

In FIG. 3, the intensity of light as measured with a photodetector and as indicated by a solid line is contrasted with the humidity in the chamber as indicated by a dashed line. Obviously, the two curves are almost identical in shape, demonstrating that the intensity of light is proportional to the humidity in air.

Figure 4:
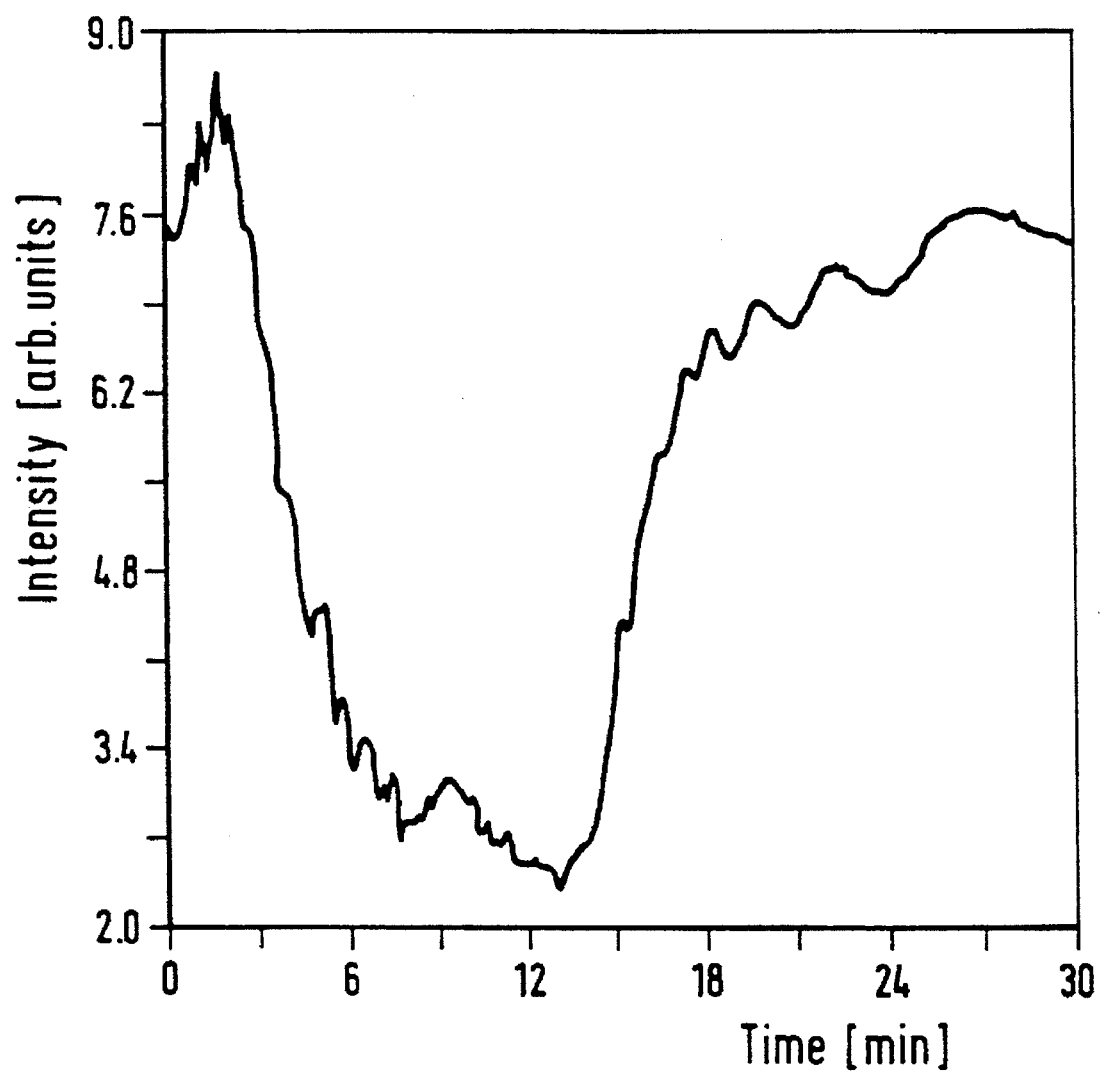
FIG. 4 is a graph showing the time response of the sensor of the invention.

FIG. 4 shows the time response of the sensor used in Example 2. When the humidity in the chamber was dropped from 60% to 30%, then raised to 60% again, the intensity of light followed the changes in humidity almost immediately. It took about three seconds for the light intensity to reach the value corresponding to the initial humidity at 60%. This time lag would probably be caused by the time necessary for dry air to replace wet air, not by the inherent time response of the sensor.

EXAMPLE 3

Figure 5:
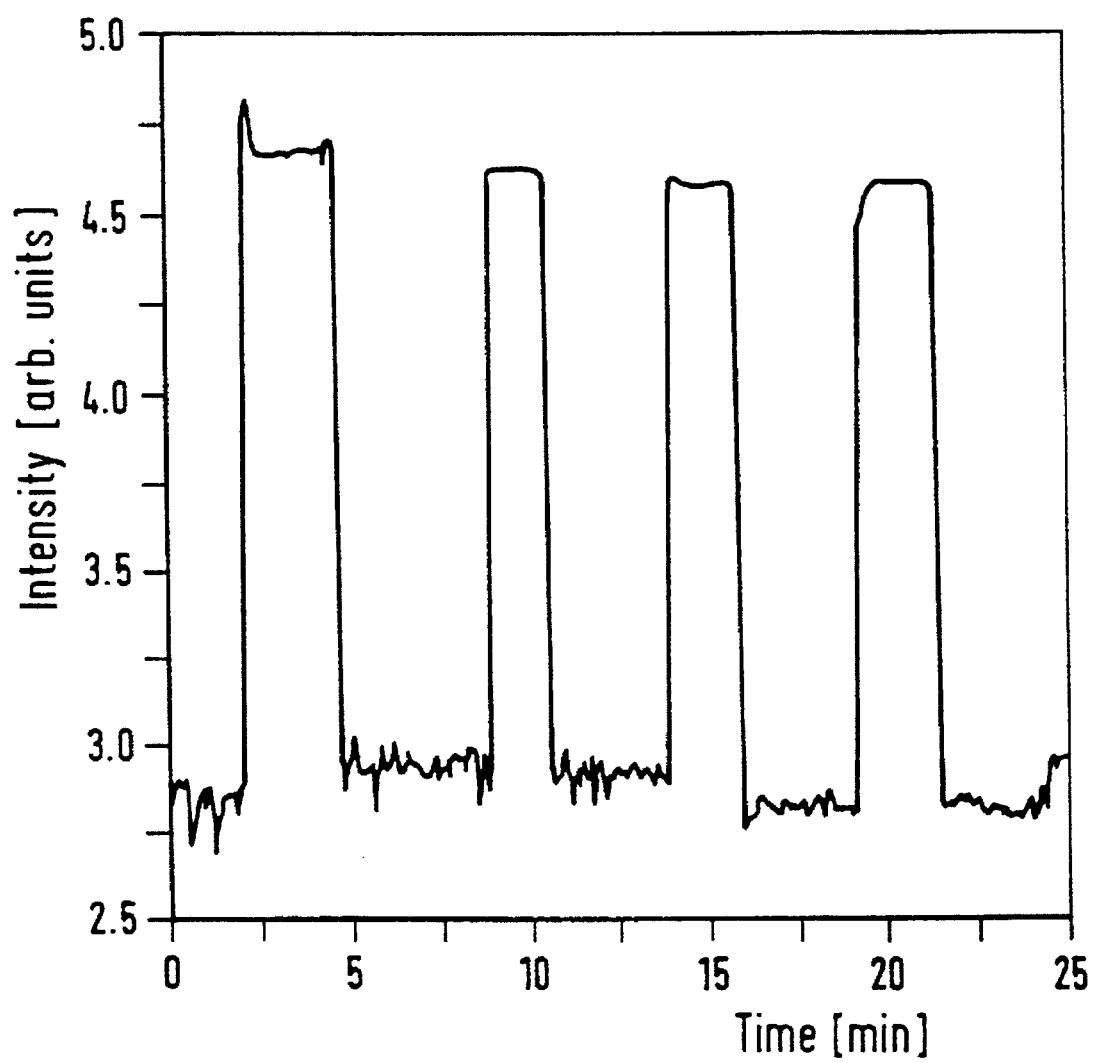
FIG. 5 is a graph showing the response of the same sensor to gasoline vapor.

In this example, gasoline detection was made using the same experimental setup as in Example 2. The result is shown in FIG. 5. When dry air (0% gasoline) and gasoline saturated air were permitted to flow over the optical sensor cyclically, the intensity of light varied accordingly in the same way. The sensor used in Example 3 had a very fast response time of only a few seconds.

What is claimed is:

1. An optical sensor for the detection of chemical species comprising an optical waveguide having a guiding thin film, wherein the thickness or the refractive index of said guiding thin film changes due to the adsorption or absorption of chemical species or the reaction of the chemical species with the guiding thin film and the thickness of said guiding thin film is above the cutoff thickness in presence of gaseous or liquid chemical species to be detected and the thickness is below the cutoff thickness in the absence of such chemical species.

2. An apparatus for the detection of chemical species comprising an array of optical sensors wherein each optical sensor of the array is as claimed in claim 1.

3. The optical sensor of claim 1 further comprising couplers for coupling light in or out of the optical waveguide, a light source for launching light into said optical sensor, at least one photodetector for detecting the intensity of the light coupled into or out of the optical waveguide, and a peripheral electric circuit connected to the photodetector.

4. The optical sensor of claim 3, wherein the peripheral electric circuit includes means for signaling the presence of a hazardous substance as detected by the sensor or means for isolating said hazardous substance.

5. The optical sensor of claim 4 wherein the hazardous substance is selected from the group consisting of toxic, burnable and flammable substances.

6. The optical sensor of claim 4 wherein the peripheral electric circuit includes means for signaling the presence of a hazardous substance and means for isolating the hazardous substance.

7. The optical sensor of claim 3 wherein the photo detectors are for detecting the intensity of light coupled into and out of the optical waveguide.

8. The optical sensor of claim 1 wherein the thickness and the refractive index of said guiding thin film changes due to adsorption or absorption of chemical species or the reaction of the chemical species with the guiding thin film.

9. The optical sensor of claim 1 wherein the optical waveguide is a planar optical waveguide.

* * * * *